United States Patent [19]

Block, Jr.

[11] Patent Number: 4,976,685
[45] Date of Patent: Dec. 11, 1990

[54] METHOD OF BLOOD-GAS INTERFACE CONTROL IN SURGICAL GAS TRAPS

[76] Inventor: Frank E. Block, Jr., 5431 Millington Rd., Columbus, Ohio 43235

[21] Appl. No.: 207,333

[22] Filed: Jun. 15, 1988

[51] Int. Cl.$^5$ ............................................. A61M 5/16
[52] U.S. Cl. ...................................... 604/52; 604/122; 604/251
[58] Field of Search ............... 604/5, 45, 49–53, 604/65, 113, 114, 122–127, 181, 93, 246, 248, 251–255, 140, 146, 183, 207, 280, 284, 405, 415

[56] References Cited

U.S. PATENT DOCUMENTS

| | | | |
|---|---|---|---|
| 3,042,038 | 3/1958 | Beacham | 604/127 |
| 3,533,400 | 10/1970 | Palich | 604/251 |
| 3,834,386 | 9/1974 | Sisley | 604/251 |
| 3,938,539 | 2/1976 | Strouth et al. | 604/127 |
| 3,939,078 | 2/1976 | Servas et al. | 604/122 |
| 3,964,479 | 6/1976 | Boag et al. | 604/251 |
| 3,976,068 | 8/1976 | Lundquist | 604/246 |
| 4,175,558 | 11/1979 | Hess et al. | 604/127 |
| 4,188,948 | 2/1980 | Swinton | 604/126 |
| 4,198,971 | 4/1980 | Noiles | 604/126 |
| 4,365,635 | 12/1982 | Bowman | 604/122 |
| 4,559,034 | 12/1985 | Krita et al. | 604/5 |
| 4,586,925 | 5/1986 | Carlsson et al. | 604/251 |
| 4,678,460 | 7/1987 | Rosner | 604/113 |
| 4,778,451 | 10/1988 | Kamen | 604/251 |

Primary Examiner—John D. Yasko
Assistant Examiner—Anthony M. Gutowski
Attorney, Agent, or Firm—Mueller and Smith

[57] ABSTRACT

Blood is stored under refrigeration at a temperature of about 4° C. When it is utilized on a relatively rapid basis within a surgical theater it is transported by tubing through a blood warming apparatus which, while warming the blood, causes an outgasing of entrained air. This air is trapped in an air trap receptacle having a drip chamber within which a gas-blood interface is developed. To assure that the capacity of the trap is not exceeded, an improved technique of gas removal and interface level setting is provided wherein access is achieved essentially through the entrance region of the gas trap receptacle.

5 Claims, 2 Drawing Sheets

METHOD OF BLOOD-GAS INTERFACE CONTROL IN SURGICAL GAS TRAPS

BACKGROUND OF THE INVENTION

Human blood or derivatives thereof is essentially universally administered to patients to treat anemia and/or blood loss when undergoing medical treatment (within surgical theaters, emergency rooms, hospital wards, and intensive care units). This blood generally is stored prior to any use in sterile polymeric receptacles or bags at about 4° C. Typically, blood and other fluids are administered through what may be a labyrinth of tubing, filters, access ports, and valving devices to the recipient, transporting of the fluids being carried out by hydrostatic pressure as developed by an elevation of the receptacle above the patient or by use of an infusion device which applies external pressure to the blood bag. The rate of administration of blood varies with the circumstances, patients undergoing general medical services on a ward or the like receiving blood at relatively slower rates, while the administration of blood units during surgery often being carried at relatively accelerated rates. In the latter surgical theaters, several units of blood may be administered at these enhanced rates. Thus, a rapid transfusion of relatively larger amounts of cold stored blood would, without correction to normal body temperatures, cause a decrease in the body temperature of the recipient. For example, a recipient weighing about 100 pounds would experience a body temperature drop of as much as 0.5° C. upon receiving a unit of blood at storage temperature. Where such a transfusion evoked hypothermia is experienced by a patient, various complications may ensue including a decrease in cardiac output, arrhythmias (and a temporary increase in serum potassium concentration). In this regard, see *Anesthesia* (Second Edition), edited by Ronald D. Miller, M.D., p. 1346, Churchill Livingstone, N.Y., 1981.

To avoid these hypothermic effects, practitioners commonly employ blood warming devices which are located (within the surgical theater) and the above-noted areas. These devices, which range from somewhat primitive warm-water baths referred to as Hemokinetotherm units to current "dry heat" warmers, serve to return blood or other fluids to a temperature of about 35° C.–40° C. in a manner non-destructive to proteins and blood cells like retained within the fluid media.

When blood at stored temperatures is rapidly warmed toward infusion temperatures by the above devices, there occurs a change in solubility characteristics of the gases which are entrained within the fluid, (particularly with respect to blood). Gas or "air" bubbles thus are formed, which, without some form of intervention, will be infused into the patient along with the administered blood. Any infusion of a large quantity of such gas or air may cause obstruction of the outflow tract of the right ventricle followed by reduction of pulmonary blood flow, and circulatory collapse. Generally, the latter condition is referred to as an air embolism which is the passage of air from the vein through the right side of the heart and the lungs, which causes pulmonary hypertension (increased pulmonary artery blood pressure) and impaired oxygen and carbon dioxide exchange across the lungs. A large air embolus can be fatal. Furthermore, fibrin may be formed on the blood-air interface of the right ventricle and then be deposited in the smaller branches of the pulmonary artery. Significant decreases in circulating platelets have been observed to be caused by air embolism. In the case of a small quantity of infused gas-air, the resultant bubbles will be trapped in the pulmonary arterial branches. Platelets may aggregate on the gas-blood interface off pulmonary arterial vessels. The passage of such bubbles also may cause pressure damage to endothelial cells in the pulmonary vaculature, resulting in deposits of fibrin on the walls of the vessel. In the above regard, see Mashimo, "Rapid Warming of Stored Blood Causes Formation of Bubbles in the Intravenous Tubing", *Anesthesia and Analgesia*, Vol. 59, No. 7, July, 1980, pp 512–513.

To avoid the above gaseous infusions of warmed blood and other intravenous fluids, practitioners now employ a cylindrical air trap within the labyrinth of distributing disposable tubing leading to the infusion point to the patient but downstream of the blood warming device. The air trap is quite simple being provided as a cylinder within which both air and blood collect, the blood being observed during an operation to drip into the chamber which, ideally, will contain about ½ fluid and ½ entrapped air or gas. By so arranging the trap such that the dripping is observable, the practitioner may be assured that blood flow is underway under the noted hydrostatic pressure. However, during the course of surgery, in many instances the amount of air-gases trapped may be in excess of the volumetric capacity of the air trap. When this occurs, the assigned personnel in surgery undertake a somewhat awkward and involved procedure in bleeding or removing air from the trap. The protocol requires that the trap be inverted with respect to its vertical sense, a syringe then is injected in a downstream port, the resultant flowing air bubble is observed as it progresses through the tubing toward the patient and is removed by hand through the syringe and needle arrangement as it reaches the air removal port. This protocal has lead to undesired incidents within the surgical theater, often results in an unwanted excursion of blood into the theater and generally represents an unsatisfactory condition.

SUMMARY

The present invention is addressed to a method and apparatus for controlling the gas-fluid interface within a gas trap as employed with an assemblage of components utilized to infuse fluids into a patient. This method achieves such control while avoiding the cumbersome procedures heretofore resorted to by medical personnel working within a surgical theater. Opportunities for accidental blood splash or spills are avoided and more accurate control is achieved with the approach of the invention.

One aspect of the invention looks to a surgical procedure of a variety wherein a supply of blood is provided from refrigerated storage for infusive application to a patient through tubing extended from the supply to a warming device, and from the warming device to a location of administration to the patient, the procedure providing a method for removing gas products resulting from the operation of the warming device which comprises the steps of:

providing a gas trap having a transparent side surface a normally upwardly disposed entrance surface in fluid flow communication with a first length of the tubing downstream from the warming device and having a lower disposed surface spaced from the entrance surface to define a gas trap chamber of given volumetric capacity and in fluid flow communication with a second length of the tubing extending from the lower disposed surface to the location of administration;

flowing the blood from the supply through the warming device, thence through the gas trap to effect an accumulation of gas and blood therein to establish a blood surface-gas interface at given levels above the lower disposed surface but spaced below the entrance surface to provide an observable quantity of collected gas products;

providing an access port to the gas trap at a select location;

accessing the accumulation of gas with a manually operated hypodermic device for applying suction from the access port when the interface level extends below an acceptable given level;

manually removing a portion of the accumulated gas in a quantity sufficient to at least restore the acceptable level with suction derived by said device; and said select location being a position next to said gas trap entrance surface effective to access said gas by said device and effect said removal thereof.

Another aspect of the invention considers an improvement in conjunction with an assemblage for administering blood from a receptacle substantially at storage temperature to a patient within a surgical theater, wherein fluid flow communication is provided with the receptacle, a blood warming device, and the place of infusion to a patient, the gas control improvement comprising a gas trap having a normally upwardly disposed entrance region, a lower disposed exit region spaced therefrom and transparent side regions therebetween defining a gas trap receptacle having a chamber of given volumetric capacity for receiving blood and gas removed therefrom by the blood warming device and effecting an accumulation of gas and blood in the cavity deriving a blood surface-gas interface at given levels above the exit region. A first tubing arrangement provides flow of blood and gas derived from the warming device to the gas trap through the entrance region. A second tubing arrangement provides flow of the accumulated blood separated from the gas trap to the place of infusion. A gas control port arrangement is positioned next to the entrance region at a location effective to provide gas exchange access with said receptacle for receiving manually applied air pressure selected from negative to positive effective to provide an adjustment of the interface to an acceptable level.

Still another aspect of the invention looks to a method for controlling the disposition of gas products resulting from the operation of a warming device which is employed in a surgical procedure wherein a supply of fluid is provided from refrigerated storage for infusive application to a patient through tubing extending from the supply to such a warming device and thence to a location of administration to the patient. The method includes the steps of:

providing a gas trap having an entrance region with a normally upwardly disposed orientation in fluid flow communication with a first length of the tubing downstream from the warming device and having a lower disposed region spaced from the entrance region to define a gas trap chamber for receiving the fluid and gas products and effecting an accumulation thereof in the chamber forming a gas-fluid interface at given levels above the exit region, the chamber being substantially transparent and in fluid flow communication with a second length of the tubing extending from the lower disposed region to the location of administration to the patient;

flowing the fluid from the supply through the warming device, thence through the gas trap cavity to effect the accumulation and establish the gas-fluid interface within the chamber at given levels above the lower disposed region but spaced below the entrance region;

providing an access port in gas transfer communication with said chamber from said entrance region;

accessing the accumulation of gas products from the access port when the gas-fluid interface is at an unacceptable level within the chamber with a hypodermic syringe; and manually applying air pressure selected in a range from negative-to-positive with said syringe to adjust the gas-fluid interface to an acceptable level while retaining said gas trap entrance region in said normally upwardly disposed orientation.

Other objects of the invention will, in part, be obvious and will, in part, appear hereinafter.

The invention, accordingly, comprises the apparatus and method possessing the construction, combination of elements, arrangement of parts, and steps which are exemplified in the following detailed disclosure. For a fuller understanding of the nature and objects of the invention, reference should be had to the following detailed description taken in connection with the accompanying drawings.

DETAILED DESCRIPTION OF THE INVENTION

Figure 1:
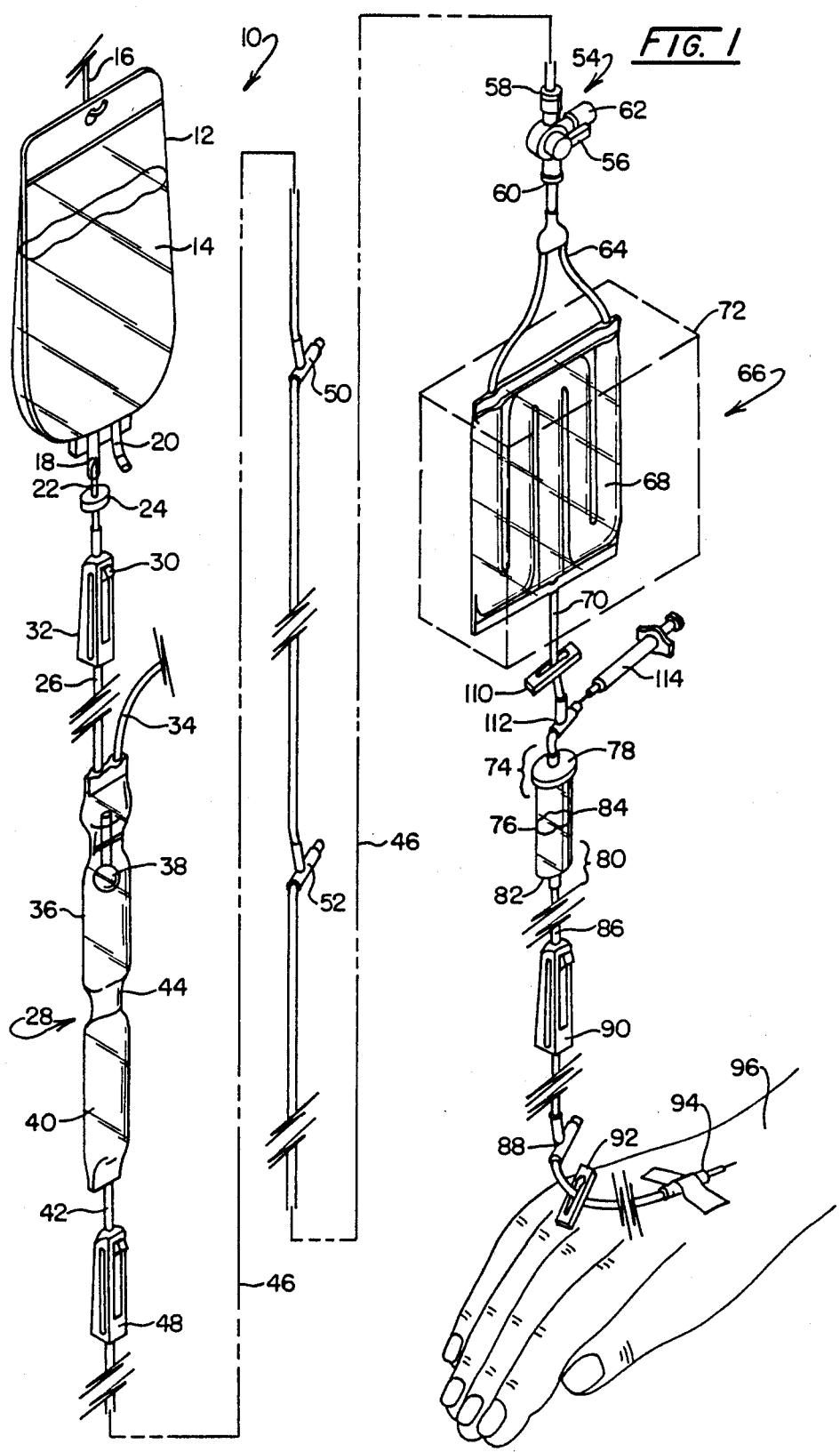
FIG. 1 is a perspective view of an assemblage of components for administering blood and other fluids to a patient in accordance with the invention, portions of the assemblage being shown schematically and in broken-away fashion in the interest of clarity.

Referring to FIG. 1, an assemblage of components typically employed within a surgical theater for administering fluids such as blood to a patient is revealed generally at 10 in partially schematic fashion. The administration of blood fluids involves a procedure wherein a unit of the blood is removed from refrigerated storage where it is retained at 4° C. and is brought to the surgical theater. The blood typically is retained in a disposable polymeric bag referred to as a "blood bag" as represented at 12. Blood bag 12 is shown carrying a quantity of blood 14 which is administered to the patient by hydrostatic pressure evolved by elevating the bag 12 a desired distance above the patient from an IV rack having a hook as at 16. Alternately the bag may be compressed by a pressuring assembly. The disposable blood bags as at 12 are generally configured having one or more fluid release ports as are represented at 18 and 20, duplicate ports being provided, inter alia, for the purpose of providing a redundancy desirable with respect to the intensity of cognizance or metal concentration within the surgical theater and, additionally, to provide an alternate injection port for the administration of medicines into the fluid 14 itself. Access port 18 is shown pierced by a hollow piercing spike 22, such insertion of the spike 22 being facilitated by an integrally formed flange 24. The opposite side of spike 22 and flange 24 is coupled in fluid communication to a length of transparent tubing 26 which extends to one input of a pump-filter assembly 28. Input to the assembly 28 may be turned off at tubing 26 by the manual movement of the roll 30 along a corresponding ramp within a roll clamp 32. Assembly 28 includes a duplicate input 34 which may be employed for attaching duplicate sources of fluid to the assemblage 10. The upwardly-disposed portion of assembly 28 at 36 functions as a manual pump which includes a ball stop 38. With the arrangement, in the course of surgery, should additional pressure be required above and beyond the hydrostatic pressure available, the portion 36 is manually grasped and squeezed, the ball 38 blocking upward movement of fluid while the pressure manually applied forces fluid downwardly into and through a filter portion of assembly 28 represented at 40. The filter 40 functions, for example, to remove any clotting blood from the system as the fluid then progresses into a next tubing component 42. Ball stop 38 serves a second function in connection with the movement of fluid through the assembly 28. In the event all fluid is utilized, the ball will drop to position 44 and block movement of air or the like into the system from the position of filter 40.

Tube 42 is somewhat lengthy, typically having an extent of about 7 feet. Thus, in the drawing, this region of tubing retained fluid flow is represented by the symbolic flow line 46. In this flow line several implements may be provided, including roller clamps as at 48 and Y-ports as at 50 and 52. These ports 50 and 52 are configured to normally pass the fluids within the flow path 46 but additionally incorporate a straight channel section having a soft protective cap thereon through which a typical hypodermic needle may be inserted. Thus, the ports may be employed for the purpose of adding medicaments in conjunction with the normal fluid flow from the supply 12. Tubing or flow path 46 is seen to terminate in a stopcock valve represented generally at 54. These valves are manually actuated by a small lever as represented at 56 to provide, for example, three-way valving activity. For example, one such path will extend from the input of the valve at 58 and pass through its normal output 60. On the other hand, an additional flow path may be developed at port 62 for receiving medicaments from the hollow stem portion of a typical hypodermic syringe. These medicaments are inserted into the normal flow of fluids which pass, as before, from the normal output 60. Output 60 is seen coupled to the dual input 64 of a blood or fluid warming assembly represented generally at 66. Some assemblages provide a single rather than a dual input as shown. Assembly 66 includes a dual path heat exchange fluid flow component 68 through which the fluid of the system passes in delay fashion, whereupon it exits at a next tubing component 70. Generally, the component 68 is retained within a blood warmer, preferably of the "dry heat" variety which is represented in phantom by block 72. In its general operation, the warming device 72 is formed of thermostatically controlled heated plates held at about 37° C.-40° C. Thus, the fluids passing through component 68 are warmed as they exit at tube 70. However, an outgasing occurs in conjunction with this warming, particularly in the case of blood fluid. For example, blood contains dissolved oxygen and carbon dioxide and when rapidly warmed toward body temperature, the resulting temperature of about 37° C. is accompanied by changes in solubility coefficients of such gases. The resultant air bubbles or gas bubbles must be removed to avoid any infusion thereof into the patient. Thus, the tubing component 70 is seen directed to the input region 74 of a gas trap receptacle 76. Recepacle 76 includes an entrance surface 78 at region 74 and extends to an exit region 80 including an exit surface 82. Intermediate the surfaces 78 and 82 there is defined a drip chamber within which fluid or blood accumulates at the lower region and gas is accumulated above that region to define a gas-liquid fluid interface 84. Interface 84 will assume various levels within the drip chamber of the receptacle 76 generally in dependence upon the amount of outgasing occuring in connection with the warming arrangement 66. Generally, the side surfaces of receptacle 76 are transparent and the dripping of fluid or blood from tube 70 thereinto provides an indicia to the practitioner that fluid is indeed flowing. As the amount of outgasing increases, however, the interface 84 will descend within receptacle 76 and, should it fall below the exit region 80 or surface 82, a resultant infusion of gas into the patient may result with the noted consequences. Thus, the practitioner observes interface 84 and as it falls below a level deemed acceptable, removal of the air component within the drip cavity must be carried out. It may be observed that the fluid flow path continues from the bottom region 80 of receptacle 76 as represented at tubing 86. This last length of tubing 86 may be of an extent amounting, for example, to about 7 feet and will include several components, for example, three Y-ports, one of which is shown at 88, a three-way stopcock valve (not shown) a roll clamp as at 90, and slide clamps as at 92 as may be appropriate. The tubing 86 terminates at a place of infusion 94 shown located at the upper hand portion 96 of a patient.

Prior to the procedure of the instant invention, the technique for controlling the interface level or amount of gas build-up within the drip cavity or chamber of receptacle 76 involved the steps of pinching off flow to the patient 94 at some position below Y access port 88; manually upturning the receptacle 76 so that the air or gas component therein now confronts lower region 80; inserting a hyopdermic syringe needle into the access leg of Y-port 88; and observing the movement of air or gas now exiting as a long bubble from lower region 80 through tubing 86. As the moving gas in tube 86 reaches the point of aspiration at port 88, negative pressure (suction) is applied from the hypodermic syringe and an appropriate amount of air or gas is removed, whereupon the receptacle 76 is returned to its upright position. Because it is desirable to observe the dripping of blood into the drip chamber of receptacle 76, not all of the gas or air is removed during this procedure. It may be apparent that the procedure is quite cumbersome and inexact.

With the procedure of the instant invention, accurate positioning of the level of interface 84 is available along with an improved technique for removing the noted gas products of the warming procedure. With the technique, flow through the upper portion of tubing 70 is stopped either by manually pinching the tubing at that location or by carrying out that same blocking function with, for example, a slide clamp as at 110. Access is made to the upper region 74 of receptacle 76 and this is shown in the figure as being provided by a Y-access port 112. With the instant procedure, the flow from the warming device 66 is terminated by activating the clamp 110 to close the tube 70 upper region and a hypodermic syringe as at 114 is inserted in the access port of Y-port 112. By withdrawing the plunger of syringe 114, negative pressure may be asserted from the access port at 112 to remove the gases above the interface 84. Additionally, positive pressure may be applied from the syringe 114 to adjust the level of the interface 84 to a desired starting level. A small amount of blood or fluid as will be contained within tubing 70 below clamp 110 is aspirated by syringe 114 with this procedure. As an alternative, an access conduit can be provided directly within the receptacle 76.

The Y-port 112 may be replaced with a stopcock similar to that at 54 to provide an arrangement wherein the needle component of syringe 114 need not be utilized. In this regard, the hollow plastic stem portion of the syringe may be inserted within the access port as at 62 of such a stopcock. It has become desirable in the surgical theater to avoid sharp needles and the like and, thus, by employing such a device as a stopcock valve, the needles may be eliminated.

Figure 2:
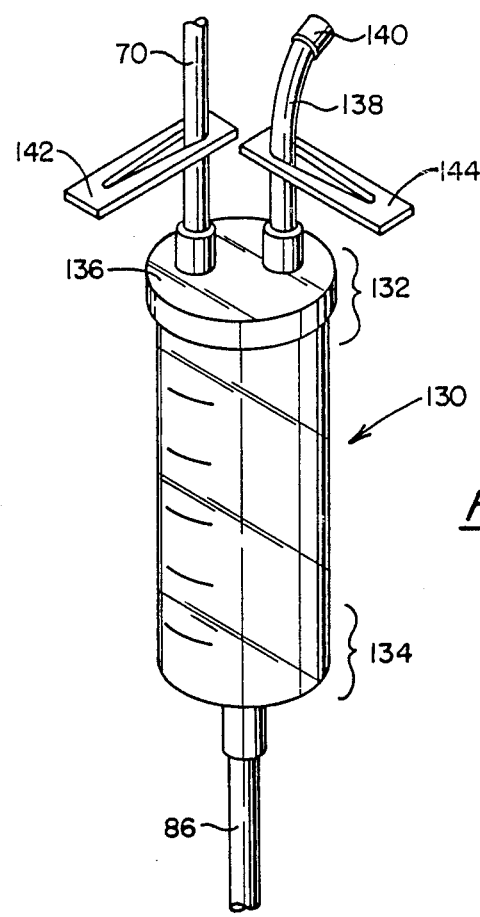
FIG. 2 is an embodiment of a gas trap and access port arrangement according to the invention.

Looking to FIG. 2, another embodiment for gas trap receptacles which may employ the technique of the invention is revealed generally at 130. Device 130 includes an upper disposed entrance region 132 as well as a lower disposed exit region 134 which may be coupled within the tubing string in the manner of receptacle 76. Accordingly, tubing component 70 is shown being directed through the entrance surface 136 of upper region 132, while, correspondingly, tube component 86 is shown being coupled in fluid flow communication with the exit surface 138 of region 134. With the instant embodiment, direct access to the upper region 132 of the drip chamber within recetacle 130 is provided by a conduit 138 located as extending through entrance surface 136 somewhat in adjacency with tubing component 70. The conduit 138 is capped at 140 such that, alternately, it may be accessed by the needle component of a hypodermic syringe as at 114 or may be accessed by the hollow stem portion thereof without employment of needles. For the latter utilization, the cap 140 is removed and access by removable association between a hypodermic hollow stem portion and component 138 is effected. To assure that no draw-down effects or the like are occasioned through component 70, the procedure in adjusting the gasfluid interface within receptacle 130 involves pinching off tubing 70. For this purpose, a conventional slide clamp as at 142 may be provided. In similar fashion, conduit 138 may be sealed by such a slide clamp as at 144. In addition to conduit structures as at 138, of course, two-way valves may be employed having a particular utilization in conjunction with hypodermic stem components as opposed to the needles thereof.

Figure 3:
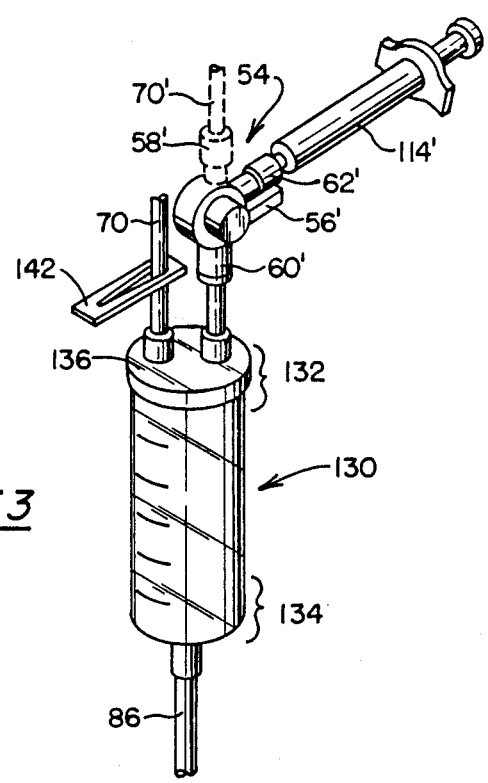
FIG. 3 is another embodiment of a gas trap and access port arrangement according to the invention.

Referring to FIG. 3, the device 130 again is reproduced as having an upper disposed entrance region 132, as well as a lower disposed exit region 134 which may be coupled within the tubing string in the manner of receptacle 76. In the latter regard, the tube component 86 is seen extending from lower disposed region 134. For one embodiment quite similar to that of FIG. 2, tubing component 70 extends through the entrance surface 136 of upper region 132. As before, a slide clamp 142 may be employed to pinch off tube 70 during level adjustment procedures. For the instant embodiment, such level adjustment procedures are provided by a valve similar to that described above in general at 54 but for the present embodiment not having an upper input port 58. The valve is seen coupled to tubing component 138 at its normal output 60'. One input to the valve at 62' is shown coupled to a hypodermic syringe 114' which is applied to the valve without a needle. Thus, the interface level within the container 130 may be adjusted at this location. As an alternate arrangement, the additional input represented at tubing component 70 and slide 142 is not provided and, as shown in phantom in the figure, the input to the valve is provided as at 58' and this input is coupled to the tubing component 70 as represented in phantom at 70'. With this arrangement, by manipulating the lever 56', input port 58' is cut off, input port 62' is then communicated with output port 60' to permit level adjustment by the application selectively of negative or positive pressure from the syringe 114'.

Since certain changes may be made in the above apparatus and method without departing from the scope of the invention herein involved, it is intended that all matter contained in the above description or shown in the accompanying drawings shall be interpreted as illustrative and not in a limiting sense.

I claim:

1. In a surgical procedure wherein a supply of blood is provided from refrigerated storage for infusive application to a patient through tubing extending from said supply to a warming device, and from said warming device to a location of administration to said patient, the method for removing gas products resulting from the operation of said warming device, comprising the steps of:

providing a gas trap having a substantially transparent side surface, a normally upwardly disposed entrance surface in fluid flow communication with a first length of said tubing downstream from said warming device and having a lower disposed surface spaced from said entrance surface to define a gas trap drip chamber of given volumetric capacity and in fluid flow communication with a second length of said tubing extending from said lower disposed surface to said location of administration;

flowing said blood from said supply through said warming device, thence through said gas trap to effect an accumulation of gas and blood therein to establish a blood surface-gas interface at given levels above said lower disposed surface but spaced below said entrance surface to provide an observable quantity of collected gas products;

providing a stopcock valve located next to said gas trap entrance surface having an externally accessible outlet port and manually actuable from a closed to an open position for forming a valve fluid passage path providing gas and liquid communication between said gas trap and said outlet port;

accessing said accumulation of gas when said interface level extends below an acceptable said given level by the removable insertion of the hollow stem component of a manually actuable syringe into said externally accessible outlet port; and manually applying suction with said syringe at said valve fluid passage path to remove a portion of said accumulated gas of quantity sufficient to at least restore said acceptable level.

2. The method of claim 1 including the step of blocking said fluid flow communication at said first length of tubing during said step of manually applying suction at said valve fluid passage path.

3. The method of claim 1 in which said stopcock valve is fixed to and extends outwardly from said entrance surface next to said first length of tubing.

4. In a surgical procedure wherein a supply of liquid is provided from refrigerated storage for infusive application to a patient through tubing extending from said supply to a warming device and thence to a location of administration to said patient, the method for controlling the disposition of gas products resulting from the operation of said warming device, comprising the steps of:

providing a gas trap having an entrance surface with a normally upwardly disposed orientation in fluid flow communication with a first length of said tubing downstream from said warming device and having a lower disposed surface spaced from said entrance region to define a gas trap drip chamber for receiving said liquid and gas products and effecting an accumulation thereof in said chamber forming a gas-liquid interface at given levels above said exit surface, said chamber being substantially transparent and in fluid flow communication with a second length of said tubing extending from said lower disposed surface to said location of administration;

flowing said fluid from said supply through said warming device, thence through said gas trap chamber to effect said accumulation and establish said gas-liquid interface within said chamber at said given levels above said lower disposed surface but spaced below said entrance surface;

providing a stopcock valve located next to said gas trap entrance surface having an externally accessible outlet port and manually actuable from a closed to an open position for forming a valve fluid passage path providing gas and liquid communication between said gas trap and said outlet ports;

accessing said accumulation of gas products by the removable insertion of the hollow stem component of a manually actuable syringe into said externally accessible outlet port when said gas-liquid interface is at an unacceptable level within said chamber with a hypodermic syringe; and manually applying air pressure selected in a range from negative-to-positive with said syringe at said valve fluid passage path in an amount effective to adjust said gas-liquid interface to an acceptable level while retaining said gas trap entrance surface in said normally upwardly disposed orientation.

5. In a surgical procedure wherein a supply of blood is provided from refrigerated storage for infusive application to a patient through tubing extending from said supply to a warming device, and from said warming device to a location of administration to said patient, the method for removing gas products resulting from the operation of said warming device, comprising the steps of:

providing a gas trap having a substantially transparent side surface, a normally upwardly disposed entrance surface in fluid flow communication with a first length of said tubing downstream from said warming device and having a lower disposed surface spaced from said entrance surface to define a gas trap drip chamber of given volumetric capacity and in fluid flow communication with a second length of said tubing extending from said lower disposed surface to said location of administration;

flowing said blood from said supply through said warming device, thence through said gas trap to effect an accumulation of gas and blood therein to establish a blood surface-gas interface at given levels above said lower disposed surface but spaced below said entrance surface to provide an observable quantity of collected gas products;

providing a stopcock valve located next to said gas trap entrance surface having a first fluid passage path communicating fluid between said warming device and said gas trap through said entrance surface and manually actuable to establish a second path providing gas and liquid communication between said gas trap and an externally accessible outlet port of said valve;

accessing said accumulation of gas by the removable insertion of the hollow stem component of a manually actuable syringe into said accessible outlet when said interface level extends below an acceptable said given level;

manually actuating said stopcock valve; and manually applying suction to said second path to remove a portion of said accumulated gas of quantity sufficient to at least restore said acceptable level.

* * * * *